United States Patent [19]

Cook et al.

[11] 4,322,227

[45] * Mar. 30, 1982

[54] GAS PURIFICATION

[75] Inventors: Charles F. Cook; George E. Hays, both of Bartlesville, Okla.

[73] Assignee: Phillips Petroleum Company, Bartlesville, Okla.

[*] Notice: The portion of the term of this patent subsequent to Dec. 16, 1997, has been disclaimed.

[21] Appl. No.: 140,629

[22] Filed: Apr. 28, 1980

Related U.S. Application Data

[63] Continuation-in-part of Ser. No. 4,789, Jan. 19, 1979, Pat. No. 4,239,510.

[51] Int. Cl.$^3$ .............................................. B01D 19/00
[52] U.S. Cl. ...................................................... 55/68
[58] Field of Search ....................................... 55/46–48, 55/68, 51

[56] References Cited

U.S. PATENT DOCUMENTS

| | | | |
|---|---|---|---|
| 1,525,060 | 2/1925 | Bertsch | 55/48 |
| 3,690,040 | 9/1972 | Halfon | 55/68 |
| 3,929,434 | 12/1975 | Nelson | 55/68 |
| 4,235,607 | 11/1980 | Kinder et al. | 55/68 |
| 4,239,510 | 12/1980 | Hays et al. | 55/68 |

*Primary Examiner*—Bernard Nozick

[57] ABSTRACT

Natural gas having a high carbon dioxide content is contacted with sea water in an absorber at or near the bottom of the ocean to produce a purified natural gas.

5 Claims, 1 Drawing Figure

GAS PURIFICATION

This application is a continuation-in-part of my copending application, Ser. No. 4,789, filed Jan. 19, 1979 now U.S. Pat. No. 4,239,510 issued 12/16/1980.

BACKGROUND OF THE INVENTION

This invention relates to a method and apparatus for treating a gaseous mixture in order to change the concentration of a component thereof. In another aspect, this invention relates to the selective absorption of an undesirable component of a gaseous mixture. In another aspect, this invention relates to an apparatus used for treating a gaseous mixture wherein said apparatus is submerged in the absorbent. Still another object of this invention relates to the contacting of an absorbent. Still another object of this invention relates to the contacting of an absorbent with a gas wherein the flow within the absorber is induced by means of the dispersion of the gas in the absorbent. In yet another aspect, this invention relates to the removal of carbon dioxide from a gas. Still another aspect of the present invention is the removal of carbon dioxide from a gas using salt water, e.g., sea water, as the absorbent. Another aspect of the present invention is the removal of carbon dioxide from carbon dioxide-containing natural gas. In yet another aspect, this invention relates to the removal of an impurity from a gas with the absorber being submerged in the absorbent and the impurity-rich absorbent is discharged at an absorbent depth such that the absorbent density at the level of discharge is very close to the density of the impurity-rich absorbent being discharged. Still another aspect of this invention relates to a method for removing impurities from a gas in which the absorbent flow rate is controlled by manipulating the liquid level in the top of the absorber. In still another aspect, this invention relates to the treatment of carbon dioxide containing natural gas obtained from an offshore well wherein the absorber is erected on the ocean floor and sea water is used to absorb the carbon dioxide.

The volume of natural and industrial gases treated for various purposes is continually increasing. Efficient and effective methods of treating gases, therefore, are very important to industry. The need for efficient and economical methods of treatment is especially important in the natural gas industry where the percentage of gas produced which requires treating will continue to increase as uncontaminated gas reserves are depleted.

One of the most common impurities found in natural gas is carbon dioxide. In many areas of the world, natural gas, predominantly methane, is found associated with major amounts of carbon dioxide. When the carbon dioxide content exceeds about 10 volume percent, especially about 20 volume percent or greater, its removal by conventional means, such as amine absorption becomes uneconomical due to the high energy consumption of the amine process required for regenerating the amine and due to the excessive size of the equipment necessary to remove such a large amount of $CO_2$. The problem also exists in the handling of the large volume of removed $CO_2$ unless a special situation exists where there is a worthwhile use for large amounts of carbon dioxide such as in flooding reservoirs for secondary or tertiary oil recovery. Also, it may be economical to use the gas as it is produced as a low heating value fuel if a suitably large demand for fuel gas for power generation or industrial purposes exists within a reasonable distance from the production site. Unfortunately, however, many of these gas reservoirs are in remote areas where no major demand for fuel exists, where carbon dioxide has no value and where construction of gas processing facilities is expensive. The cost of transporting the gas can be reduced, therefore, if the $CO_2$ could be removed at the well, especially if the $CO_2$ is present in a very high concentration.

Accordingly, it is an object of this invention to provide a method which enables more economical and convenient treating of gaseous mixtures.

Another object of the present invention is to provide an apparatus to be used in the treatment of gaseous mixtures.

Another object is to provide a process for treating a gas with an absorbent which does not require mechanical pumping of the absorbent or a high pressure absorber vessel.

Another object of the present invention is to provide a simple process for treating natural gas obtained from off shore wells.

Another object of the present invention is to save on cost of transporting gas from a well in a remote area, e.g., such as an offshore well 200 miles from land.

Another object is to provide a novel means for achieving a single stage of contacting of absorbent sea water with $CO_2$-rich natural gas in a cocurrent flow contactor.

Other objects, aspects, and the several advantages of this invention will be apparent to those skilled in the art upon a study of this disclosure, the appended claims and the drawing.

SUMMARY OF THE INVENTION

The present invention is concerned with a process for treating a gaseous mixture in order to change the concentration, i.e., remove a component or impurity thereof. The impurity is removed through selective absorption. A gas and absorbent are contacted in a cocurrent contacting zone wherein the flow of the absorbent is induced by means of the dispersion of the gas in the absorbent.

In accordance with this invention the preferred embodiment resides in a process for removing $CO_2$ from natural gas. The process of this invention comprises the withdrawal of natural gas containing 20° to 95 volume percent $CO_2$ from a natural gas well and passing this gas into an absorber which is located at or near the bottom of the ocean. Sea water from the ocean in the vicinity of this absorber is then introduced into the absorber and contacted in this absorber with the natural gas containing the high quantity of $CO_2$. Thereby, a purified natural gas having reduced carbon dioxide content as compared to the natural gas coming from the well is produced as well as $CO_2$ rich sea water.

The absorption is generally carried out at a temperature in the range of 30° to 80° F. Preferably and advantageously, the inside pressure in the absorbing zone and the pressure of the surrounding ocean are approximately the same. Therefore, the construction of the absorber can be relatively inexpensive since no high pressure stability is required. Furthermore, it is presently preferred to also utilize any natural pressure of the natural gas for providing the energy to move the fluids through the process unit.

In one embodiment, this invention is concerned with a method for removing at least one impurity from a gas comprising introducing an absorbent having an absorbing capacity for an impurity and a gas into the lower portion of an absorber's contacting zone, wherein the absorber is submerged in the absorbent, to thereby allow contact between the gas and absorbent as the gas and absorbent flow cocurrently upward through the absorber. Unabsorbed gas is accumulated near the top of the absorber and recovered. Impurity-rich absorbent is then discharged into the surrounding absorbent via appropriate discharge means.

Another embodiment of the invention concerns the discharge of the impurity-rich absorbent into the surrounding absorbent depth such that the absorbent density at the level of discharge is very close to, but preferably, less than the density of the impurity-rich absorbent being discharged.

In another embodiment, the absorbent flow rate through the absorber is controlled by manipulating the liquid level in the top of the absorber, thereby changing the liquid head against which the absorbent must flow.

The invention is especially applicable to any carbon dioxide-containing gas, but is particularly useful when the carbon dioxide concentration is 10 volume percent or more. When the system is used for the removal of carbon dioxide from a gas, salt water, e.g., sea water, can be used as an appropriate absorbent.

Accordingly, the process and apparatus of the present invention find great applicability in the treatment of a gaseous mixture of carbon dioxide and natural gas where the natural gas well is in a remote area with sea water available. The invention would be of particular importance in treating natural gas having a high concentration of carbon dioxide obtained from an offshore well.

The apparatus generally used in the process of the invention comprises a contacting zone with means for introducing feed gas and absorbent into the bottom portion of the contacting zone with means near the top of the zone for collecting and removing unabsorbed gas.

In another embodiment, the absorber also comprises a plurality of discharge means located at various levels to thereby allow the discharge of the impurity-rich absorbent at a depth such that the absorbent density at that level is very close to but, preferably less than the density of the impurity-rich absorbent being discharged. The absorber also comprises means to transport impurity-rich absorbent from the upper portion of the contacting zone to the discharge means.

BRIEF DESCRIPTION OF THE DRAWING

The FIGURE is a schematic of a specific embodiment of the invention.

DETAILED DESCRIPTION OF THE INVENTION

Figure 1:
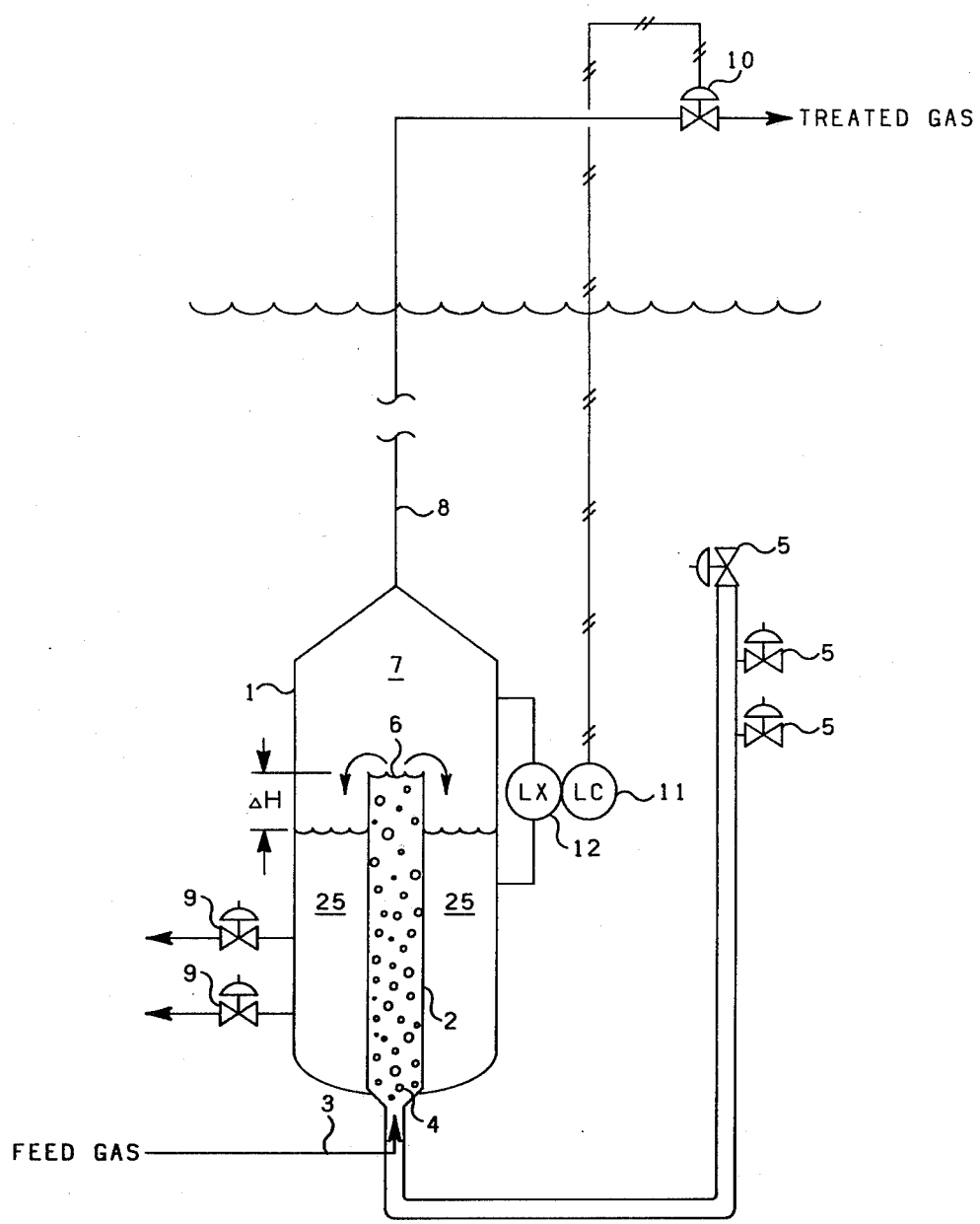

Treatment of a gaseous mixture by an absorbent in order to remove an undesirable component thereof is well known in the art. The present invention, however, provides a novel means for achieving contacting of an adsorbent with a gas in a cocurrent flow contactor.

The absorber of the present invention comprises a contacting zone with means for introducing feed gas and absorbent into the lower portion of the contacting zone and accumulating means near the top of the contacting zone for collecting and removing unabsorbed gas. Any suitable accumulating means for collecting and removing the unabsorbed gas that is known in the art can be used in the present invention, e.g., a vapor-liquid separator or even an inverted funnel type structure wherein the gas is collected in the cone and removed by means of a conduit to appropriate storage for further use. The absorber is generally submerged in the absorbent at a sufficient depth to obtain the hydraulic pressure desired in order to maintain sufficient absorber pressure to thereby avoid mechanical pumping of absorbent and the need for a high pressure absorber vessel since internal and external pressures would therefore nearly be the same.

The lower portion of the contacting zone into which the absorbent and gas are introduced can also comprise the dispersion means. The dispersion means can be any conventional dispersion device, e.g., a bank or plurality of orifices, or, a plurality of Venturi tubes. The dispersion device aids in dispersing the gas as bubbles into the absorbent which thereby aids in the contacting between the gas and absorbent and in inducing the flow of the absorbent upwardly through the contacting zone.

The absorber can also comprise a plurality of discharge means located at various levels of the absorbent to thereby allow the discharge of the impurity-rich absorbent at an absorbent depth such that the absorbent density at that level is very close to, but, preferably, less than the density of the impurity-rich absorbent being discharged. It is preferred, therefore, that the impurity-rich absorbent is discharged at an absorbent depth such that the absorbent density at that level is at least about 0.0002 g/ml less than the density of the impurity-rich absorbent being discharged. This insures that the impurity-rich absorbent sinks and does not rise to the surface of the body of the absorbent. If the impurity-rich absorbent is discharged at an absorbent depth at which the absorbent density is greater than that of the impurity-rich absorbent, bubbles of impurity can form and pass from solution. This is particularly important when $CO_2$ is being absorbed by sea water as it is not desirable to allow the $CO_2$ to come out of solution and pass into the atmosphere. It is preferable to have the $CO_2$ rich sea water sink and have the $CO_2$ remain subsurface so that the $CO_2$ is gradually dissipated, e.g., by ocean currents. The depth at which the impurity-rich absorbent is discharged, however, should not be at such a shallow depth as to allow mixing with fresh absorbent to be used in the separation process.

Passage means allow the impurity rich absorbent to flow from the contacting zone to the appropriate level of discharge. The passage means can be nothing more than an annulus between the contacting zone and an extended portion of the collecting means as shown in the FIGURE at 25. The annulus is formed by the extension of the lower portion of the collecting means for the unabsorbed gas. The lower portion extends outside of the contacting zone and below the lowest level at which effluent absorbent is likely to be discharged. The plurality of discharge means can be located vertically on the extended lower portion of the collecting means, which can also be referred to as the outside shell of the absorber.

In another embodiment, the absorber can have a plurality of inlet means of different absorbent depths to thereby allow taking of absorbent of various densities and conduit means for transporting the absorbent from the plurality inlet means to the bottom portion of the contacting zone. The plurality of inlet means provides for selecting the desired absorbent density, and, for example, allows for the inlet of the absorbent to be from a depth where the absorbent density is less than that of the impurity-rich absorber effluent and is still above the depth at which impurity-rich absorbent is discharged. This prevents the mixing of impurity-rich absorber effluent with absorbent to be used in the contacting zone.

The process generally comprises introducing a gas and an absorbent having an absorbing capacity for an impurity contained in said gas into the lower portion of an absorber's contacting zone to thereby allow contacting between the gas and absorbent as the gas and absorbent flow cocurrently upward through the absorber. The absorber is generally submerged in the absorbent, e.g., sea water, at a sufficient depth to obtain the hydraulic pressure desired to maintain absorber pressure sufficient to thereby avoid mechanical pumping of the absorbent. The need for a high pressure absorber vessel is also avoided since internal and external pressures are nearly the same due to the submergence of the absorber in the absorbent. When the absorbent and gas reach the top of the contacting zone, unabsorbed gas is accumulated near the top of the absorber in an accumulating means and recovered therefrom. The impurity-rich absorbent that issues from the top of the contacting zone is then discharged from the absorber into the surrounding absorbent via discharge means.

The flow of the absorbent in the absorber is induced by means of the dispersion of the gas in the absorbent when being introduced into the cocurrent contacting zone. The feed gas is injected into the lower portion of the contacting zone which can comprise a conventional dispersion device such as a bank or plurality of orifices or a plurality of venturi tubes. The orifices or other dispersion means can be positioned across the entire cross section of the lower portion of contacting zone to insure the uniform dispersion of gas bubbles in the absorbent. The dispersion of the gas into the lower portion of the contacting zone induces the absorbent flow through the contacting zone and the buoyancy resulting from the feed gas being dispersed in the liquid in the contacting zone provides for continued absorbent circulation. This portion of the system, basically, operates on the same principle as an airlift pump.

The discharge means used to discharge the impurity rich absorbent into the surrounding absorbent can be any appropriate means for allowing the used absorbent to pass from the absorber. For example, the discharge means can merely be an opening in the absorber located near the upper portion of the absorber. Passage means can also be used to pass the impurity-rich absorbent to a desired depth of absorbent prior to being discharged into the surrounding absorbent. It is preferred that impurity-rich absorbent effluent from the absorber is discharged at a depth such that the absorbent density at that level is very close to, but, less than the density of the impurity-rich effluent which thereby minimizes the chance for impurity-rich absorbent to back mix with fresh absorbent entering at the base of the absorber. Preferably, the impurity-rich absorbent effluent from the absorber is discharged at a depth such that the absorbent density at that level is at least about 0.0002 g/ml less than the density of the impurity-rich absorbent being discharged. The discharge of the used or impurity-rich absorbent at a depth of surrounding absorbent that is of a lesser density also avoids the release of large volumes of absorbed impurities to the atmosphere in the vicinity of the operation. This is especially desirable when the absorbed impurity is carbon dioxide as it is undesirable to release large volumes of carbon dioxide to the atmosphere in a single location. Furthermore, the $CO_2$ will not have a tendency to rise and contaminate fresh sea water to be used in the separation process, which sea water is taken at a lesser depth than that at which the $CO_2$-rich sea water is discharged. The $CO_2$, rather, will remain in solution at a low depth and gradually be dispersed by ocean currents. The invention, therefore, has special applicability when sea water is being used to absorb the carbon dioxide from natural gas.

When the impurity-rich absorbent passes through a passage means prior to being discharged into the surrounding absorbent, the absorbent flow rate can be controlled by manipulating the liquid level in the top of the absorber, thereby changing the liquid head ($\Delta H$, see figure) against which the absorbent must flow. The difference in the levels between the impurity-rich absorbent in the passage means and the absorbent in the contacting zone is controlled to thereby control the absorbent flow rate. A small $\Delta H$, indicating a high level of impurity rich absorbent in the passage means, encourages greater absorbent flow, whereas a high $\Delta H$, indicating a low level of impurity rich absorbent in the passage means, causes reduced absorbent flow. Besides the level control, the absorbent flow rate can be controlled by other conventional methods such as the use of a pressure controller to control the back pressure of the treated gas or by just monitoring and controlling the rate at which the treated gas is taken off. Generally, any conventional method of controlling the rate of absorbent flow can be used to obtain and maintain the desired rate.

Although it is generally desired to have a high absorbent flow, the rate of flow of the absorbent must be balanced against the practical aspect that too high an absorbent flow can dissolve too much of the gas and thereby give a low measure of recovery, e.g., this is true when sea water is being used to absorb carbon dioxide or some other impurity from natural gas. A high absorbent flow also affects the density of the impurity-rich absorbent as the concentration of impurity, e.g., $CO_2$, would be less. This would require discharging the $CO_2$-rich absorbent at a less dense or shallower level which can increase the chances of back-mixing with fresh absorbent to be used in the separation process.

The process and apparatus can be employed for the treatment and removal of components or impurities from any gas that contains components which are to be removed and are more soluble in the solvent than the other components of the gas. Natural gas, nitrogen, hydrogen, and many other synthesis, refinery, and manufactured gases can be treated by the process in order to remove impurities such as carbon dioxide, hydrogen sulfide, carbon monoxide, sulfur dioxide, and ammonia, to name a few. The type of absorbent used and the conditions of the treatment will vary, however, with the particular gases treated and particular impurities one wishes to remove. For example, the invention can be used to remove water-soluble gases from gases insoluble in water by using water as the absorbent. When a particular component of the gas is chosen as the component to be removed, an appropriate absorbent is chosen which has an affinity for the component but in which the other components are insoluble.

The processs and apparatus are particularly useful for the treatment of a carbon dioxide-containing gas for the removal of carbon dioxide. The invention is applicable to any carbon dioxide-containing gas, but will be particularly economical when the $CO_2$ concentration is about 10, and especially 20, volume percent or more.

The use of salt water, e.g., sea water can be used most economically and efficiently as the absorbent for carbon dioxide from a carbon dioxide-containing gas. Although other appropriate absorbents can be used, the particular type of absorbent used will ultimately be determined by the gas, which must be less soluble than the $CO_2$ in the absorbent, in admixture with the carbon dioxide.

The invention has been found to be particularly useful in the removal of carbon dioxide from natural gas, especially, when the natural gas field is in a remote area and the $CO_2$ concentration is 10 volume percent or more of the gas mixture. The removal of the carbon dioxide, when it is in such high concentrations, at the well will help reduce the cost of transporting the gas from the remote area to a place of use or storage. The invention, therefore, finds great applicability to the treatment of natural gas obtained from a gas well located at sea, e.g., 200 miles from land, as the pumping of the gas to land for processing will be a great expense and the removal of carbon dioxide, which can be about 70 mole percent of the gas mixture, will help to reduce the cost of transporting the gas to shore.

The invention does not require that the apparatus be used at sea, but can be also used in fresh or brackish water areas as long as the apparatus can be completely submerged. In shallow water areas, a hole can be dug in the bottom of the reservoir in order to completely submerge the column to provide greater hydrostatic operating pressure for the apparatus. In general, the hydrostatic operating pressure can be increased to the desired level if the body of absorbent is of insufficient depth by digging a hole in the floor of absorbent body.

The invention is also applicable for use in a large pool or tank of solvent or absorbent in which the contacting device is completely submerged. Once the absorbent is introduced into the device and gas is introduced into the bottom of the device, the hydraulic lift is sufficient so that no other pumps are needed to effect the cocurrent contacting.

One preferred embodiment of this invention, however, is the use of the process and apparatus to treat natural gas obtained from an off shore well at sea for the removal of carbon dioxide using the sea water as an absorbent. The $CO_2$ removal is accomplished by erecting the cocurrent absorption towers on the ocean floor and using the surrounding sea water as the absorbent. The location on the ocean floor is not essential. As long as the column is completely submerged, it can be suspended or supported or can even rest in a hole of sufficient size bored into the bottom of the water reservoir in order to provide sufficient hydrostatic operating pressure for the process.

The invention, therefore, provides a novel means for achieving a single stage of contacting of absorbent sea water with $CO_2$-rich natural gas in a cocurrent flow contactor. If more than one stage of contacting is desired multiple stage contacting can be obtained by introducing the treated gas removed from the top of one absorber into the bottom of another similar absorber.

Better understanding of the invention will be obtained by reference to the drawing and the following illustrative example. The drawing and illustrative examples are used as a detailed description of one preferred embodiment of the invention but is not meant to be limited thereto. Although the process is described with respect to the removal of carbon dioxide from natural gas using sea water as the absorbent, it is to be noted that the invention is not meant to be limited to this one preferred embodiment.

Referring now to the FIGURE, the absorber is submerged in the sea at any desired level, but could most conveniently be located on or near the sea floor. The outer shell of the absorber, which is an extension of the means for accumulating the treated gas, can be closed at the bottom as illustrated, e.g., sealed to the draft tube contacting zone 2. Alternatively, the bottom of the outer shell can be open. The extension or skirt, however, should extend well below the lowest level at which effluent sea water is likely to be discharged. Feed gas, at near absorption temperature and at slightly higher pressure than the base of the absorber to thereby provide the energy for dispersion, is injected 3 into the contacting zone, inducing the flow of sea water into the bottom of the contacting zone 4 by virtue of the buoyancy created by the column of dispersed gas bubbles. A dispersion means can be used to aid in dispersing the feed gas into the liquid in the contacting zone.

Inlet sea water to be used as absorbent is preferably taken at a depth where water density is less than the $CO_2$-saturated effluent to thereby avoid possible mixing of the effluent water with the fresh water. Thus, the inlet will generally be at a shallower depth than the depth at which the effluent is discharged, hence, several inlet valves 5 can be provided at different water depths to allow for taking inlet sea water of such a lesser density. Absorbent sea water can be taken from any depth, however, as long as one is careful to avoid the problem of mixing the discharge with the inlet sea water.

As the mixed phases issue from the top of the draft tube contacting zone 6 into the means for accumulating the treated gas 7, the unabsorbed gas is disengaged and accumulated in 7 and is then removed from the top of the absorber via conduit means 8. The $CO_2$-rich sea water flows into a passage means and is then discharged into the ocean via a discharge line located at appropriate depth. In the drawing, the passage means is an annular space 25 between the contacting zone and the outer shell or extension of the accumulating means. The $CO_2$ rich sea water is then discharged via one of the plurality of discharge means 9. If desired, fresh sea water can be introduced into the discharge line by means not shown to lower the $CO_2$ concentration of the effluent, thereby assuring that gas bubbles are not released from the effluent stream. If fresh sea water is used to lower the $CO_2$ concentration of the effluent, the level of discharge should be such that the density of the effluent is greater than that of the surrounding sea water, even upon temperature equilibration with the surrounding sea water.

The liquid level at the top of the absorber, or the $\Delta H$, can be controlled in order to obtain the desired sea water flow rate or any conventional method can be used to control the sea water flow rate. One manner in which this can be done is by manipulating a control valve 10 on the treated gas effluent, thereby changing the gas back pressure. If desired, a pressure controller, not shown, can be provided on the discharge gas line 8 or a level controller 11 and level transmitter 12 can be used to manipulate valve 10. The sea water flow rate can be measured by any conventional means or the flow can be estimated indirectly by monitoring the composition of the treated gas with a conventional onstream analyzer, e.g., a gas chromatograph. The liquid level in the absorber can be either above or below the top of the draft tube contacting zone depending on flow conditions and the particular equipment configuration.

The desired level of discharge of the $CO_2$-rich sea water can be determined by comparing the density profile of the surrounding sea with the density of the $CO_2$-saturated effluent using conventional density measuring devices or simply by determining the temperature profile of the sea, the temperature and composition of the effluent water and comparing these with known density-temperature relationships. Dissolved $CO_2$ tends to increase the density of sea water. For example, at 80° F., sea water densitites are as follows:

| d, gm/ml | $CO_2$ Partial Pressure, psia |
|---|---|
| 1.010426 | 0 |
| 1.010634 | 15 |
| 1.010762 | 20 |
| 1.010850 | 25 |
| 1.010880 | 30 |

The density of sea water also tends to increase with decreasing temperature, of course, and the temperature of sea water decreases with increasing water depths. Thus, other things being equal, the more $CO_2$ enriched the effluent sea water becomes the deeper the point of discharge would be.

The level of $CO_2$-enriched sea water discharge can be controlled in a variety of ways. The preferred manner of control is that of using discharge lines at two or more levels from the absorber, as indicated at 9 in the FIGURE. These would preferably be remotely operated. The operation can even be automated by using a differential density instrument which can compare the density of the effluent water with that of the surrounding sea at appropriate levels. The level of sea water discharge can also be varied by using a movable or telescoping discharge means, e.g., a pipe or some other conduit, which can be pneumatically manipulated.

The following example illustrates the utility of the invention and exemplifies the type of conditions used in the process of the invention. The example, however, is not meant to be limiting in any way as the conditions under which the process can run can vary greatly and depend upon, among other things, the location of the apparatus, the particular absorbent used and the gaseous mixture to be treated. The particular example is concerned with the preferred embodiment of the invention wherein the single stage absorber is submerged in sea water for the purpose of removing carbon dioxide from methane gas.

EXAMPLE

Natural gas comprising 70 percent by volume $CO_2$ and 30 percent $CH_4$ is produced at a rate of 18,000,000 SCFD (standard cubic feet per day) from well heads as deep as 450 feet below mean sea level at a pressure of 3,000 psig and a temperature of 260° F. (127° C.) Sea floor temperature is about 60° F. The gas is passed to a 40-foot single stage absorber as shown in the FIGURE. The pressure at the bottom of the absorber is about 210 psia with the pressure at the top of the absorber about 198 psia. The gas is contacted with the absorbent sea water in a 30-foot draft tube-type contacting zone.

The following table gives information with respect to the amount of $CO_2$ absorbed.

|  | Case I | Case II |
|---|---|---|
| Sea water absorbent circulation | 36,000 gpm (80 ft³/s) | 72,000 gpm (160 ft³/s) |
| $CO_2$ final concentration (% volume) | 42% | 25% |
| $CO_2$ removed (% volume) | 73% | 90% |
| $CH_4$ removed (% volume) | 11% | 28% |

Certain modifications of the invention will become apparent to those skilled in the art, and the illustrative details enclosed are not to be construed as imposing unnecessary limitations on the invention.

We claim:

1. A process for removing at least one impurity from a gas comprising
   (a) withdrawing natural gas containing 10 volume percent or more carbon dioxide from a natural gas well,
   (b) passing the natural gas into an absorber located at or near the bottom of the ocean, wherein the pressure inside said absorber is approximately equal to the pressure of the ocean surrounding said absorber,
   (c) withdrawing sea water from the ocean in the vicinity of said absorber and introducing the sea water withdrawn into said absorber,
   (d) contacting said natural gas in said absorber with said sea water withdrawn to produce purified natural gas with reduced carbon dioxide content as compared to the natural gas coming from said well and $CO_2$-rich sea water,
   (e) accumulating said purified natural gas near the top of said absorber for recovery,
   (f) and recovering said purified natural gas from said absorber.

2. A process in accordance with claim 1 wherein said natural gas comprises from 20 to 95 volume percent carbon dioxide.

3. Process in accordance with claim 1 comprising passing said purified natural gas from said absorber to a processing unit.

4. Process in accordance with claim 1 wherein the absorption is carried out at a temperature in the range of 30° to 80° F.

5. A process in accordance with claim 1 wherein said $CO_2$-rich sea water is discharged from said absorber into the surrounding ocean at a depth where the density of the surrounding sea water is less than the density of the $CO_2$-rich sea water being discharged.

* * * * *